United States Patent [19]

Quackenbos et al.

[11] Patent Number: 4,794,265
[45] Date of Patent: Dec. 27, 1988

[54] SURFACE PIT DETECTION SYSTEM AND METHOD

[75] Inventors: George S. Quackenbos, Newburyport, Mass.; Jay L. Ormsby, Salem, N.H.; Eric T. Chase, Andover, Mass.; Sergey V. Broude, Acton, Mass.; Koichi Nishine, Westford, Mass.

[73] Assignee: QC Optics, Inc., Burlington, Mass.

[21] Appl. No.: 47,889

[22] Filed: May 8, 1987

[51] Int. Cl.[4] .......................................... G01B 21/88
[52] U.S. Cl. .................................. 250/572; 356/430; 356/237
[58] Field of Search ............... 250/562, 563, 572, 571; 356/446, 448, 237, 430, 431

[56] References Cited

U.S. PATENT DOCUMENTS

| | | | |
|---|---|---|---|
| 4,172,666 | 10/1979 | Clarke | 250/563 |
| 4,184,082 | 1/1980 | Peoples | 356/446 |
| 4,492,477 | 1/1985 | Leser | 250/572 |
| 4,583,861 | 4/1986 | Yamaji et al. | 356/446 |
| 4,598,997 | 7/1986 | Steigmeier et al. | 250/572 |

Primary Examiner—Edward P. Westin
Assistant Examiner—Khaled Shami
Attorney, Agent, or Firm—Joseph S. Iandiorio; Douglas E. Denninger

[57] ABSTRACT

An apparatus and method for uniquely detecting pits on a smooth surface by irradiating an area of the surface; separately sensing radiation scattered from the surface in the near-specular region indicative of a pit and in the far-specular region indicative of a flaw and producing signals representative thereof; normalizing the near-specular signal with respect to the far-specular signal to indicate a pit; and discriminating the near-specular components of the normalized signal representative of surface pits.

21 Claims, 4 Drawing Sheets

SURFACE PIT DETECTION SYSTEM AND METHOD

FIELD OF INVENTION

This invention relates to an optical detection technique for uniquely detecting surface pits on a smooth surface.

BACKGROUND OF INVENTION

There is a significant quality control problem associated with a class of surface imperfections known as surface pits. This typically occurs, for example, on nickel-plated aluminum substrates to be used in the manufacture of thin-film magnetic media, but may be a problem with respect to any smooth surface. Such depressions or pits are but one class of flaws that can be encountered. Other classes of flaws include defects large and small and contamination such as dirt, dust, oil, fingerprints and the like. Defects on the surface of rigid magnetic media are a result of an impingement onto the surface or a tearing of material away from the surface. These types of defects can be very large scratches or gouges on the surface or very small (5 μm and smaller) tears or pricks on the surface. The pits are a local depression or bump with a diameter of from ten to several hundred micrometers with a depth of one-tenth to one micron, typically. The pits themselves may be smooth or contain breaks such as craters in their surface. Presently quality control inspection is effected by human operators who are subject to a number of shortcomings. They are slow and incompatible with automated equipment; they are unable to reliably, repeatedly detect very small pits and to distinguish them from other defects.

SUMMARY OF INVENTION

It is therefore an object of this invention to provide an improved technique for detecting pits in surfaces.

It is a further object of this invention to provide such a technique which is fast, reliable, and repeatable.

It is a further object of this invention to provide such a technique which can be accomplished automatically.

It is a further object of this invention to provide such a technique which discriminates between pits and other surface flaws such as defects and contamination.

It is a further object of this invention to provide such a technique which permits quantification of detected pits.

The invention results from the realization that pits produce radiation scattering primarily in the near-specular region, while the other types of flaws, primarily defects, produce radiation scattering primarily in the far-specular region, and that the two regions can be optically discriminated, and further that the far-specular region information can be used to normalize the near-specular region information and thereby further enhance the detection of pits.

This invention features a detection system for uniquely defining pits on a smooth surface. There are means for directing a beam of radiation to a surface and means for separately sensing radiation scattered from the surface in the near-specular region and in the far-specular region and producing signals representative thereof. There are means responsive to the means for sensing for normalizing the near-specular signal with respect to the far-specular signal to provide a normalized near-specular signal, and means for discriminating the near-specular components of the normalized signal representative of surface pits.

The invention also features an optical detection device for uniquely detecting pits on a smooth surface, including means for directing a beam of radiation to a surface and means for sensing radiation scattered frmm the surface in only the near-specular region indicative of a surface pit.

In preferred embodiments the means for sensing includes lens means and a radiation source. The radiation source may provide a coherent beam and may in fact be a laser source There may be means for providing relative motion between the beam and surface. The motion may be provided in two directions relative to one another: one motion may be rotational and the other translational. The means for sensing include means for separating the radiation scattered in the near-specular region from the other radiation and a sensor for receiving the near-specular scattered radiation and producing a signal representative thereof. The means for separating may include means for directing specular radiation to one destination, far-specular radiation to a second destination, and near-specular radiation to the sensor.

The invention also features a detector apparatus for uniquely defining pits on a smooth surface. It includes means for separately sensing radiation scattered from the surface in the near-specular region and in the far-specular region and producing signals representative thereof. There are means responsive to the means for sensing for normalizing the near-specular signal with respect to the far-specular signal to provide a normalized near-specular signal. There are means for discriminating the near-specular components of the normalized signal representative surface pits. The means for separately sensing may include a first sensor for sensing near-specular radiation and a second sensor for sensing far-specular radiation. The normalizing means may include a comparator and the comparator may receive the near-specular signal as a first polarity and the far-specular signal as a second, opposite polarity and sum the two signals. The comparator may subtract the near-specular signal from the far-specular signal.

The means for discriminating may include a first detector circuit for detecting components of the first polarity of the normalized signal. There may also be means for discriminating the far-specular components of the normalized signal representative of other surface flaws, and that may include a second detector circuit for detecting components of the second polarity of the normalized signal. There may be a size determination circuit for classifying the near-specular component of the normalized signal into one of a plurality of sizes and there may be means for locating the position of the pit represented by the near-specular component of the normalized signal.

The invention also features a method of uniquely detecting pits on a smooth surface including irradiating an area of a surface and then separately sensing radiation scattered from the surface in the near-specular region indicative of a pit and in the far-specular region indicative of a flaw and producing signals representative thereof. The near-specular signal is normalized with respect to the far-specular signal, and then the near-specular components of the normalized signal are discriminated to provide a signal representative of surface pits.

DISCLOSURE OF PREFERRED EMBODIMENT

Other objects, features and advantages will occur from the following description of a preferred embodiment and the accompanying drawings, in which.

Figure 1:
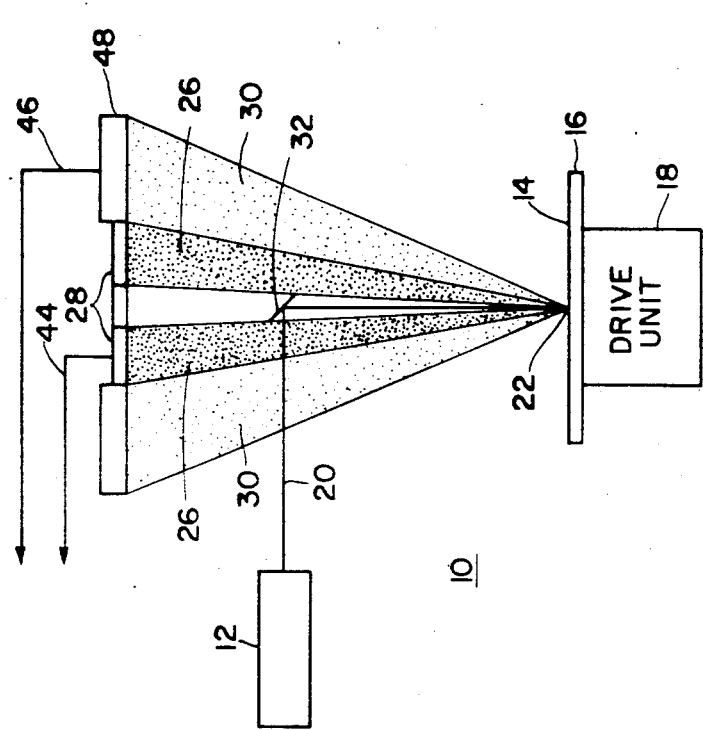
FIG. 1 is a schematic diagram of an optical detection device according to this invention.

There is shown in FIG. 1 an optical detection device 10 according to this invention which includes a means 12 for directing a beam of radiation onto the surface 14 to be inspected of a magnetic storage disk 16. Disk 16 is mounted for movement in two mutually perpendicular directions in the plane of the surface 14. In this way the spot 22 formed by beam 20 is made to move relative to surface 14. Since surface 14 is smooth, typically a highly polished or specular surface, it normally reflects the radiation of beam 20 back along beam 20. However, if a pit is encountered, light is scattered, not greatly into the far-specular region, but rather in the near-specular region as shown by volume 26, generally conical in shape and in the nature of a toroid where it approaches sensor 28. Other types of flaws, such as defects and contamination, also scatter the light but into the far-specular region such as indicated by conical volume 30. The realization that the pits scatter the light predominantly in the near-specular region enables the use of a sensor such as sensor 28 properly placed to be used to detect the occurrence of pits on surface 14. By near-specular region is meant an angle of approximately 40-100 milliradians. By far-specular region is meant an angle greater than 100 milliradians. While the beam 20 is shown as normal to surface 14, this is not necessary as any angle between grazing and normal would suffice. Mirror 32 is sized and positioned so that it directs beam 20 to surface 14 and with respect to the return radiation blocks virtually only the specular reflection from surface 14 while leaving the volume 26 surrounding it free to pass the near-specular scattered radiation.

Figure 2:
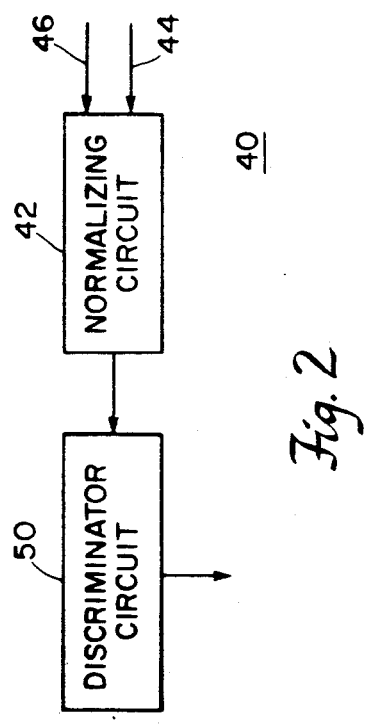
FIG. 2 is a block diagram of a detection apparatus according to this invention.

The detector apparatus 40, FIG. 2, according to this invention includes a normalizing circuit 42 which receives the output from sensor 28 on line 44 representing the near-specular signal representative of a pit, and the signal on line 46 from a similar sensor 48 which provides a signal representative of the far-specular radiation in the conical volume 30. Typically the normalizing circuit 42 enhances the signal-to-noise ratio from approximately 2:1 to a range of 30-40:1. The output from normalizing circuit 42 is delivered to discriminator circuit 50 which detects the component of the normalized signal which epresents the near-specular signal. That component may then be used to trigger alarms or displays as explained infra.

Figure 3:
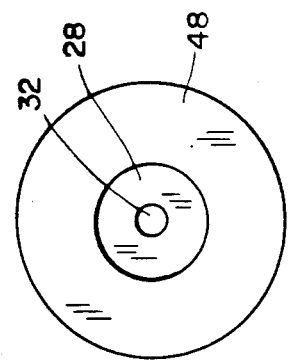
FIG. 3 is a top plan view showing the detectors of FIG. 1.

A top view of sensors 28 and 48 of FIG. 1 is shown in FIG. 3, where the toroidal shape is readily apparent.

Figure 4:
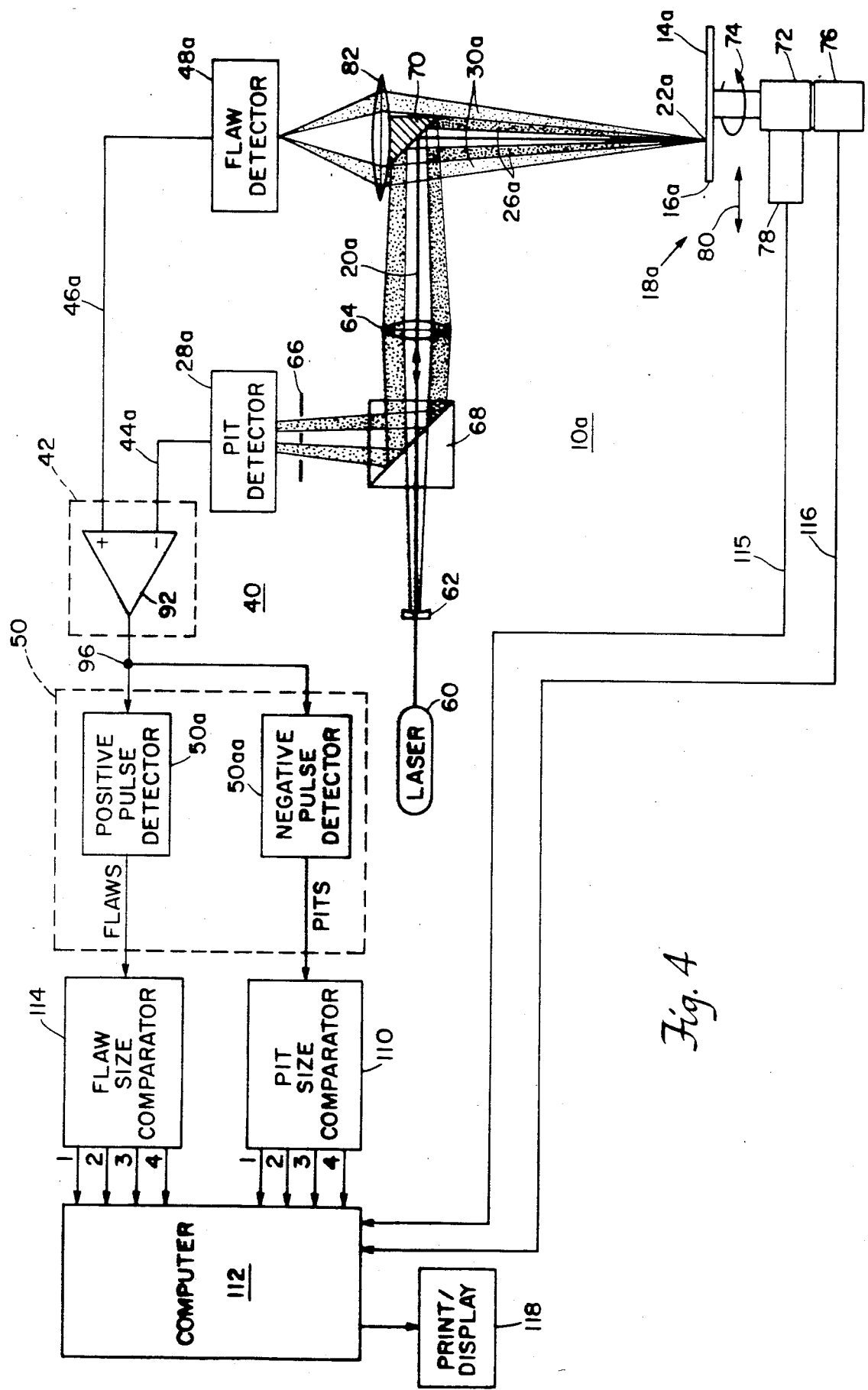
FIG. 4 is a more detailed block diagram showing a system including an optical detection device and detection apparatus in accordance with this invention.

In a preferred construction, FIG. 4, optical detection device 10a includes a light source which may be but need not be a collimated, coherent light source such as laser 60, whose output is fed through beam expander 62 and then focussing lens 64 to create beam 20a which strikes corner mirror 70. The beam is then reflected down to a spot 22a on the surface 14a of disk 16a. Disk 16a is mounted on an air spindle 72 which rotates disk 14a as indicated by arrow 74. An encoder 76 monitors and controls the rotation of air spindle 72. A servo drive 78 moves air spindle 72 in a translational manner back and forth in the direction shown by arrow 80. Some of the radiation striking a surface depression or pit at spot 22a is reflected, in the near-specular region 26a. Radiation in this region encounters the surface of corner mirror 70 and is reflected back to the surface of beam splitter 68 and towards the pit detector 28a. The specular reflection and scattered radiation in the near-specular region 26a are redirected toward the spatial filter 66 which blocks the specular reflection, while the scattered radiation in the near-specular region 26a passes on to the pit detector 28a which provides a signal indicative of the near-specular region radiation.

If at spot 22a there is another type of flaw as well, such as a defect, then the radiation returns primarily in the far-specular region 30a, which surrounds and avoids corner mirror 70 and instead is focussed by lens 82 on flaw detector 48a which provides a signal representative of the light scattered in the far-specular region.

There are many other constructions which can be used in place of the optical detector 10a, FIG. 4. For example, beam splitter 68 can be a mirror with a hole centered around the illuminating beam 20a to further restrict the light and enhance the signal-to-noise ratio.

Figure 5:
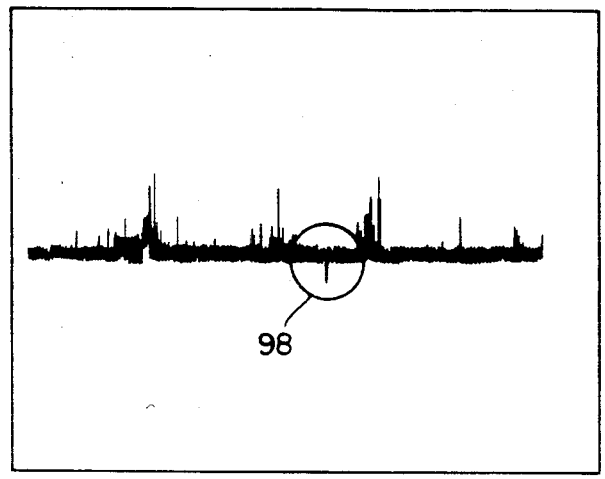
FIG. 5 is a photograph of a normalized signal obtained from one complete rotation at a single radius of the surface to be inspected.

The signal representative of the near-specular region and the pits is fed on line 44a to the negative input of amplifier 92, while the signal representative of the far-specular region radiation indicative of other defects is fed on line 46a to the positive input of amplifier 92. In amplifier 92 the two signals are algebraically summed: that is, the pit signal is subtracted from the flaw signal and the resultant signal is provided at the output to positive pulse detector 50a and negative pulse detector 50aa. The normalized output of amplifier 92 for one complete rotation of disk 16a at a single fixed radius is shown in FIG. 5. This is the signal that appears at junction 96 in FIG. 4. The single negative pulse 98 represents a pit. The multitude of positive-going background pulses represent any one of a number of other flaws including defects and contamination and noise.

Figure 6:
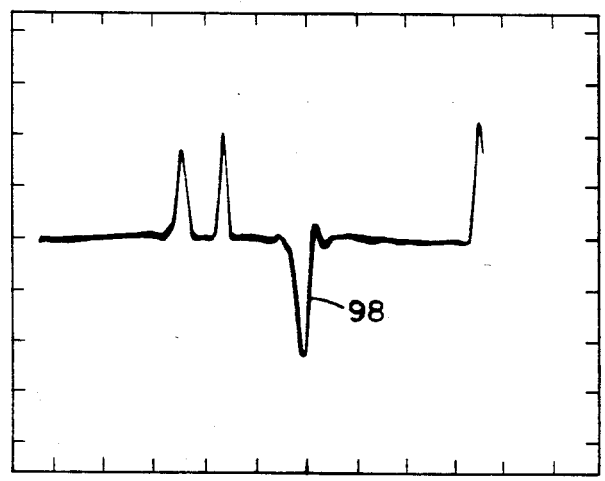
FIG. 6 is an enlarged view of the circled portion of the signal in FIG. 5.
Figure 7:
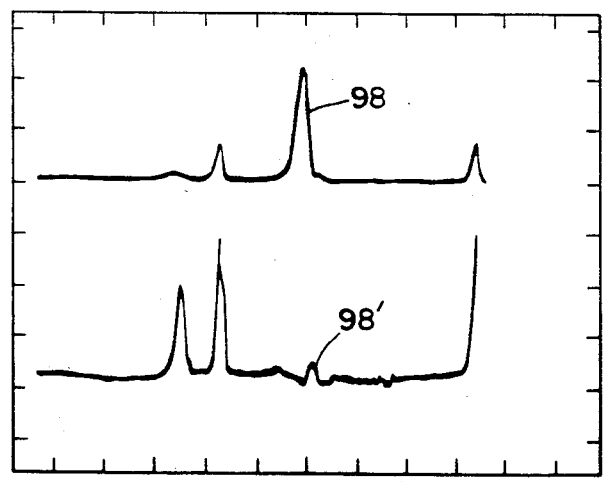
FIG. 7 is an enlarged view of the pit signal and flaw or defect signal which are normalized to obtain the normalized signal in FIG. 6.

An enlargement of the circled area in FIG. 5 is shown in FIG. 6, where the negative-going pulse 98 is more clearly shown along with the neighboring positive-going pulses. The section of the normalized signal shown in FIG. 6 is formed from the two signals shown in FIG. 7. The upper trace is the pit signal on line 44a from pit detector 28a. The lower trace is the output on line 46a from flaw detector 48a. It is the summation of these two signals that produce the signal shown in FIG. 6. It can be seen that the peak 98 in the upper trace of FIG. 7 is detected as quite large in the near-specular radiation, while the same pit produces a much lower peak 98' in the lower trace. This verifies that the dominant radiation scattering for pits occurs in the near-specular region, not the far.

With the signal of FIG. 5 present at junction 96, negative pulse detector 50aa, which may be a rectifier or diode, easily detects the pit 98 and provides a signal representative thereof to the pit size comparator 110. The pit size comparator classifies the signal into one of four sizes and indicates that size to computer 112. Positive pulse detector 50a may be provided to similarly detect positive-going peaks representative of other defects on the surface which may be delivered to a flaw size comparator 114 which classifies the signal in a similar way and delivers it to computer 112. The amplitude of the pit signal delivered to pit size comparator 110 is determined in part by the curvature of the pit. With this system, pits as small as 5μ may be detected and other defects as small as 0.5μ may be detected. In comparison, an operator with even the best eyesight can see pits only as small as approximately 10–20μ and other defects only as small as approximately 3–5μ.

Computer 112 drives servo device 78 and receives positional input from it over line 115, and drives encoder 76 and receives positional information from it on line 116 so that a printout or display may be provided at 118, which indicates the radius and angle at which a pit or defect or other flaw was found and the size of the pit or defect classified from 1 through 4. For example, a typical printout for a pit derived from pit size comparator 110 appears as follows:

| # | RADIUS (mils) | THETA (deg.) | Size |
| --- | --- | --- | --- |
| 1 | 802.00 | 289 | 4 |
| 2 | 802.50 | 289 | 4 |
| 3 | 802.50 | 289 | 4 |
| 4 | 803.00 | 289 | 4 |
| 5 | 803.00 | 289 | 4 |
| 6 | 803.50 | 289 | 4 |
| 7 | 803.50 | 289 | 4 |
| 8 | 804.00 | 289 | 4 |
| 9 | 804.50 | 289 | 1 |
| 10 | 1259.00 | 23 | 1 |
| 11 | 1259.00 | 49 | 2 |
| 12 | 1259.50 | 49 | 1 |
| 13 | 1368.50 | 94 | 2 |
| 14 | 1369.00 | 94 | 2 |
| 15 | 1801.00 | 306 | 1 |

Figure 9:
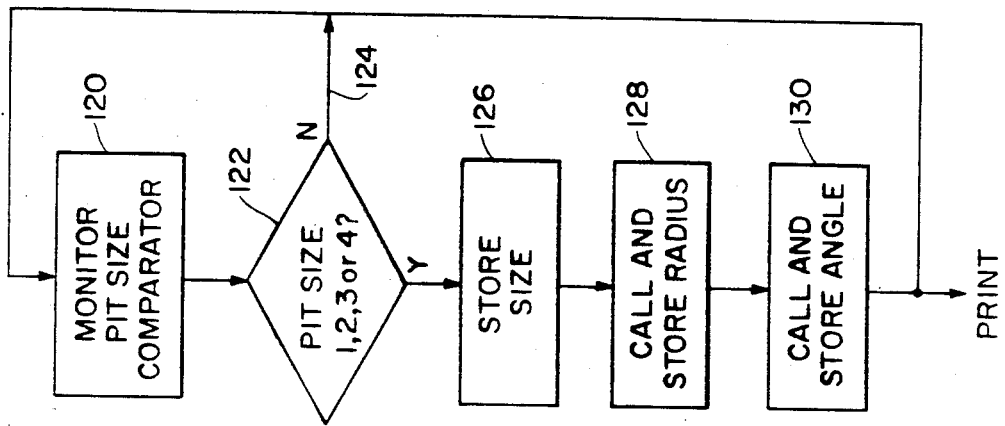
FIG. 9 is a flow chart showing the routine used to obtain the map of FIG. 8.
Figure 8:
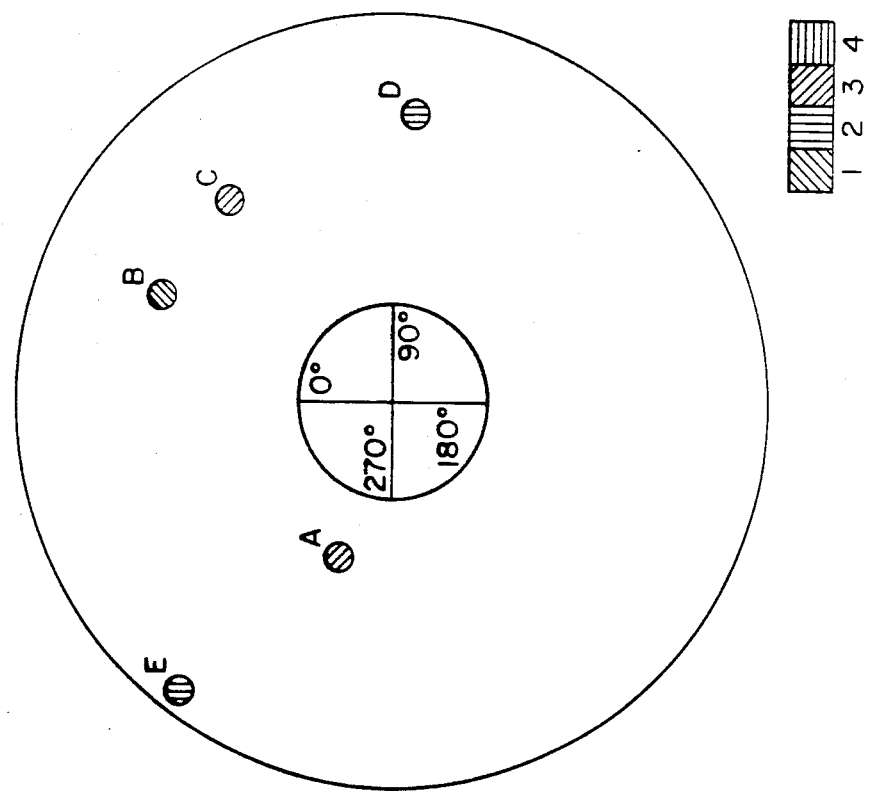
FIG. 8 is a plan view showing a pit map of a disk produced by the system of this invention.

It can be seen from this chart that the multiple pit detections 1–9 indicate a single pit at an angle of 289° (pit A) which extends from a radius of 802 mils to 804.5. Single pits are also indicated by multiple pit detections 11 and 12 (pit C) and pit detections 13 and 14 (pit D). Single pits are indicated by single pit detection #10 (pit B), and pit detection #15 (pit E). The numbers #10 and #15 refer to the chart shown above. For further convenience, the pit detections may be displayed on a map of the disk surface as shown in FIG. 8, where each of the circles represents a detected pit and the crosshatching indicates the size, 1, 2, 3 or 4, as indicated by the key in the lower right-hand corner of FIG. 8. The chart and the mapping in FIG. 8 may be simply accomplished with computer 112 by programming it to effect a routine such as shown in FIG. 9, where the computer in step 120 constantly monitors the pit size comparator 110. If the pit size does not reach a level 1 in step 122, then the system is rerouted on line 124 back to the input of step 120. If a pit size of 1 or larger is encountered, the computer then in step 126 orders that the size be stored and that the present radius and angle be called and stored in steps 128 and 130. This information can then later be printed out as in the chart or in the map of FIG. 8 and then attached to the inspected workpiece to accompany it through the rest of the manufacturing process.

The apparatus disclosed illustrates one implementation for the method of this invention. According to the method, a beam of radiation is directed to a surface to be inspected. The radiation scattered from the surface is sent to the near-specular region and the far-specular region to produce signals representative thereof. The near-specular signal is normalized with respect to the far-specular signal. The near-specular components of the normalized signal are then discriminated to provide signals representative of surface pits.

Although specific features of this invention are shown in some drawings and not others, this is for convenience only as each feature may be combined with any or all of the other functions in accordance with the invention.

Other embodiments will occur to those skilled in the art and are within the following claims.

What is claimed is:

1. A detection system for uniquely defining pits on a smooth surface comprising:

means for directing a beam of radiation to a surface;

means for separately sensing radiation scattered from the surface in the near-specular region and in the far-specular region and producing signals representative thereof;

means, responsive to said means for sensing, for normalizing the near-specular signal with respect to the far-specular signal to provide a normalized near-specular signal; and means for discriminating the near-specular components of said normalized signal representative of surface pits.

2. The device of claim 1 in which said means for directing includes lens means and a radiation source.

3. The device of claim 2 in which said radiation source provides a collimated beam.

4. The device of claim 2 in which said radiation source provides a coherent beam.

5. The device of claim 2 in which said radiation source is a laser.

6. The device of claim 1 further including means for providing relative motion between said beam and the surface.

7. The device of claim 6 in which said means for providing relative motion moves said beam and surface in two directions relative to one another.

8. The device of claim 7 in which said means for providing relative motion includes means for rotating said surface and translating said surface relative to said beam.

9. The device of claim 1 in which said means for sensing includes means for separating radiation scattered in the near-specular region from other radiation and a sensor for receiving said near-specular scattered radiation and producing a signal representative thereof.

10. The device of claim 9 in which said means for separating includes means for directing specular radiation to one destination, far-specular radiation to a second destination and near-specular radiation to said sensor.

11. A detector apparatus for uniquely defining pits on a smooth surface, comprising:

means for separately sensing radiation scattered from the surface in the near-specular region and in the far-specular region and producing signals representative thereof; and means, responsive to said means for sensing, for normalizing the near-specular signal with respect to the far-specular signal to provide a near-specular signal; and means for discriminating the near-specular components of said normalized signal representative of surface pits.

12. The device of claim 11 in which said means for separately sensing includes a first sensor for sensing near-specular radiation and a second sensor for sensing far-specular radiation.

13. The device of claim 11 in which said means for normalizing includes a comparator.

14. The device of claim 13 in which said comparator receives said near-specular signal as a first polarity and said far-specular signal as a second opposite polarity and sums the signals.

15. The device of claim 13 in which said comparator subtracts said near-specular signal from said far-specular signal.

16. The device of claim 14 in which said means for discriminating the near-specular components includes a first detector circuit for detecting components of said first polarity of said normalized signal.

17. The device of claim 11 further including means for discriminating far-specular components of said normalized signal representative of other surface flaws.

18. The device of claim 14 further including means for discriminating far-specular components of said normalized signal representative of other surface flaws, said means for discriminating the far-specular components including a second detector circuit for detecting components of said second polarity of said normalized signal.

19. The device of claim 11 further including a size determination circuit for classifying the near-specular component of said normalized signal into one of a plurality of sizes.

20. The device of claim 11 further including means for locating the position of the surface pit represented by said near-specular component of said normalized signal.

21. A method of uniquely detecting pits on a smooth surface, comprising:
   irradiating an area of a surface;
   separately sensing radiation scattered from the surface in the near-specular region indicative of a pit and in the far-specular region indicative of a flaw and producing signals representative thereof;
   normalizing the near-specular signal with respect to the far-specular signal; and
   discriminating the near-specular components of the normalized signal representative of surface pits.

* * * * *